US006368826B1

(12) United States Patent
Ligensa et al.

(10) Patent No.: US 6,368,826 B1
(45) Date of Patent: Apr. 9, 2002

(54) IGF-1 RECEPTOR INTERACTING PROTEINS

(75) Inventors: Tanja Ligensa, Lohmar; Ralf Schumacher; Michael Weidner, both of Penzberg, all of (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/453,195

(22) Filed: Dec. 2, 1999

(30) Foreign Application Priority Data

Dec. 3, 1998 (EP) .............................. 98122992

(51) Int. Cl.⁷ .......................... C12P 21/06; C12N 15/00; C12N 5/00; C07H 21/04

(52) U.S. Cl. .................. 435/69.1; 435/320.1; 435/325; 536/23.5

(58) Field of Search ............................. 435/69.1, 320.1, 435/325; 536/23.5

(56) References Cited

U.S. PATENT DOCUMENTS 2,915,082 A    12/1959    Shaw

FOREIGN PATENT DOCUMENTS

| EP | 063 879  | 11/1982 |
| EP | 128 018  | 12/1984 |
| EP | 173 251  | 3/1986  |
| EP | 200 362  | 12/1986 |
| WO | 89/06698 | 7/1989  |
| WO | 95/14772 | 6/1995  |
| WO | 97/27296 | 7/1997  |

OTHER PUBLICATIONS

Stratagene 1993 Product Catalog, p. 43.*
NCI–CGAP, GenBank Accession No. AA515857, Nov. 13, 1997.*
Wang and Strittmatter, GenBank Accession No. AF061623, Nov. 10, 1998.*
De Vries et al., GenBank Accession No. AF089816, Oct. 24, 1998.*
De Vries et al., GenBank Accession No. AFO89817, Oct. 24, 1998.*
Lin et al., J. Exp. Clin. Cancer Res., vol. 15, pp. 319–326 (1996).
van der Laan et al., Thyroid, vol. 5, No. 1, pp. 67–73 (1995).
Rousset et al., Oncogene, vol. 16, pp. 643–654 (1998).
De Vries et al., Proc. Natl. Acad. Sci. USA, vol. 95, pp. 12340–12345 (1998).
No. XP–002102461, Database EMBL ID AF 032120, Bunn et al., "Cloning and Characterization of GLUT1CBP, a Novel PDZ domain–containing Protein that Binds Specifically to the GLUT1 Tansporter C–terminus" (1998).
No. XP–002102452, Abstract of Bunn et al., "Identification and Characterization of a Novel Glucose Transporter Binding Protein" (1997).
No. XP–002102462, Database EMBL ID AF061262 (1998).
Lamothe et al., Gene, vol. 182, pp. 77–80 (1996).
Dey et al., Gene, vol. 209, pp. 175–183 (1998).
Baserga, Trends in Biology, vol. 14, pp. 50–152 (1996).
Baserga, Perspective in Cancer Research, vol. 55, pp. 249–252 (1995).
Atschul et al., J. Mol. Biol., vol. 215, pp. 403–410 (1990).
Atschul et al., Nucleic Acids Res., vol. 25, pp. 3389–3402 (1997).
Bates et al., Br. J. Cancer, vol. 72, pp. 1189–1193 (1995).
Behrens et al., Nature, vol. 382, pp. 638–642 (1996).
Behrens et al., Science, vol. 280, pp. 596–599 (1998).
Burfeind et al, Proc. Natl. Acad. Sc. USA, vol. 93, pp. 7263–7268 (1996).
Büttnet et al., Mol. Cell. Biol., vol. 11, pp. 3573–3583 (1997).
Cabral et al., Nature, vol. 382, pp. 649–652 (1996).
Chomczynski et al., Anal. Biochem., vol. 162, pp. 156–159 (1987).
Chowdhury et al., Mech. Dev., vol. 39, pp. 129–142 (1992).
Cooke et al., New Biol., vol. 1, pp. 66–74 (1989).
Denny et al., Gene, vol. 106, pp. 221–227 (1991).
Dey et al., Mol. Encocrinol., vol. 10, pp. 631–641 (1996).
Feinberg et al., Anal. Biochem., vol. 137, pp. 266–267 (1984).
Fields et al., Nature, vol. 340, pp. 245–246 (1989).
Goulding et al., EMBO J., vol. 10, pp. 1135–1147 (1991).
Harrington et al., EMBO J., vol. 13, pp. 3286–3295 (1994).
He, W., et al., J. Biol. Chem., vol. 271, pp. 1641–11645 (1996).
Kalebic et al., Cancer Research, vol. 54, pp. 5531–5534 (1994).
Kaleko et alk, Mol. Cell. Biol., vol. 10, pp. 464–473 (1990).
Lamothe et al., FEBS Lett., vol. 373, pp. 51–55 (1995).
Lehmann et al., Nucleic Acids Res., vol. 18, pp. 1048 (1990).
Margolis et al., Proc. Natl. Acad. Sc. USA, vol. 89, pp. 8894–8898 (1992).
Morrione et al., J. Virol., vol. 69, pp. 5300–5303 (1995).
Morrione et al., Cancer Research, vol. 56, pp. 3165–3167 (1996).
Needleman et al., J. Biol. Chem., vol. 48, pp. 443–453 (1970).
Pearson, Methods in Enzymology, Academic Press, San Diego, CA, USA, vol. 183, pp. 63–68 (1990).
Ponting et al., BioEssays, vol. 19, pp. 469–479 (1997).

(List continued on next page.)

Primary Examiner—Yvonne Eyler
Assistant Examiner—Janet L. Andres
(74) Attorney, Agent, or Firm—George W. Johnston; Dennis P. Tramaloni; F. Aaron Dubberley

(57) ABSTRACT

The invention comprises a nucleic acid molecule with the sequence SEQ ID NO:5 and the complementary sequence, and its use in diagnosis and therapy. This nucleic acid molecule (IIP-10) is a gene which encodes an IGF-1 receptor binding polypeptide.

5 Claims, 5 Drawing Sheets

OTHER PUBLICATIONS

Figure 1A:
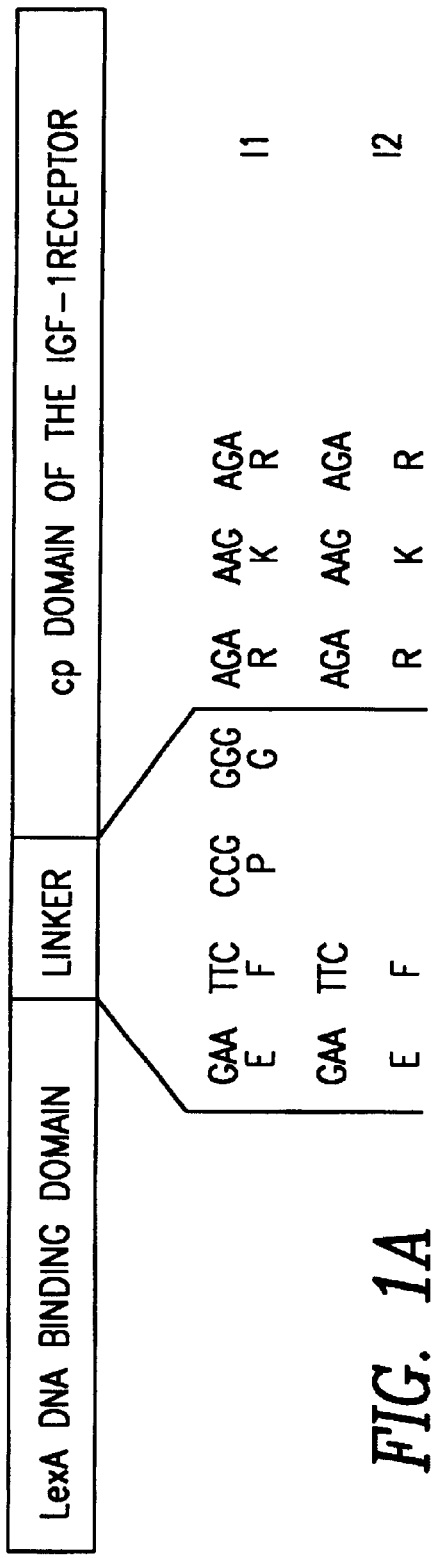

Prager et al., *Proc. Natl. Acad. Sci. USA*, vol. 91, pp. 2181–2185 (1994).
Quinn et al., *J. Biol. Chem*, vol. 271, pp. 11477–11483 (1996).
Resnicoff et al., *Cancer Research*, vol. 54, pp. 2218–2222 (1994).
Resnicoff et al., *Cancer Research*, vol. 54, pp. 4848–4850 (1994).
Resnicoff et al., *Cancer Research*, vol. 55, pp. 2463–2469 (1995).
Resnicoff et al., *Cancer Research*, vol. 55, pp. 3739–3741 (1995).
Reidel et al., *J. Biochem*, vol. 122, pp. 1105–1113 (1997).
Rocchi et al., *Endocrinology*, vol. 137, pp. 4944–4952 (1996).
Rogler et al., *J. Biol. Chem.*, vol. 269, pp. 13779–13784 (1994).
Sell et al., *Cancer Research*, vol. 55, pp. 303–305 (1995).
Sell et al., *Mol. Cell. Biol.*, vol. 14, pp. 3604–3612 (1994).
Sell et al., *Proc. Natl. Acad. Sci. USA*, vol. 90, pp. 11217–11221 (1993).
Singleton et al., *Cancer Research*, vol. 56, pp. 4522–4529 (1996).
Smith et al., *Adv. Appl. Math.*, vol. 2, pp. 482–489 (1981).
Tartare–Deckert et al., *Endocrinology*, vol. 137, pp. 1019–1024 (1996).
Tartare–Deckert et al., *J. Biol. Chem.*, vol. 270, pp. 23456–23460 (1995).
Trojan et al., *Science*, vol. 259, pp. 94–97 (1993).
Ullrich et al., *EMBO J.*, vol. 5, pp. 2503–2512 (1986).
Wahl et al., *Proc. Natl. Acad. Sci. USA*, vol. 76, pp. 3683–3687 (1979).
Wang et al., *J. Biol. Chem.*, vol. 273, pp. 3136–3139 (1998).
Weidner et al., *Nature*, vol. 384, pp. 173–176 (1996).
Yokouchi et al., *Oncogene*, vol. 15, pp. 7–15 (1998).

* cited by examiner

Fig. 5

```
  1  MSRPRKRLAG TSGSDKGLSG KRTKTENSGE ALAKVEDSNP QKTSATKNCL

51  KNLSSHWLMK SEPESRLEKG VDVKFSIEDL KAQPKQTTCW DGVRNYQARN

101  FLRAMKLGEE AFFYHSNCKE PGIAGLMKIV KEAYPDHTQF EKNNPHYDPS

151  SKEDNPKWSM VDVQFVRMMK RFIPLAELKS YHQAHKATGG PLKNMVLFTR

201  QRLSIQPLTQ EEFDFVLSLE EKEPS*
```

▶ putative N-glycosylation site

◆ putative Casein kinase II phosphorylation site

● putative N-myristoylation site

∨ putative Tyrosine kinase phosphorylation site

✦ putative Protein kinase C phosphorylation site

↔ putative NLS

IGF-1 RECEPTOR INTERACTING PROTEINS

BACKGROUND OF THE INVENTION

The IGF-1 receptor signaling system plays an important role in tumor proliferation and survival and is implicated in inhibition of tumor apoptosis. In addition and independent of its mitogenic properties, IGF-1R activation can protect against or at least retard programmed cell death in vitro and in vivo (Harrington et al., *EMBO J.* 13 (1994) 3286–3295; Sell et al., *Cancer Res.* 55 (1995) 303–305; Singleton et al., *Cancer Res.* 56 (1996) 4522–4529). A decrease in the level of IGF-1R below wild type levels was also shown to cause massive apoptosis of tumor cells in vivo (Resnicoff et al., *Cancer Res.* 55 (1995) 2463–2469; Resnicoff et al., *Cancer Res.* 55 (1995) 3739–3741). Overexpression of either ligand (IGF) and/or the receptor is a feature of various tumor cell lines and can lead to tumor formation in animal models. Overexpression of human IGF-1R resulted in ligand-dependent anchorage-independent growth of NIH 3T3 or Rat-1 fibroblasts and inoculation of these cells caused a rapid tumor formation in nude mice (Kaleko et al., *Mol. Cell. Biol.* 10 (1990) 464–473; Prager et al., *Proc. Natl. Acad. Sci. USA* 91 (1994) 2181–2185). Transgenic mice overexpressing IGF-II specifically in the mammary gland develop mammary adenocarcinoma (Bates et al., *Br. J. Cancer* 72 (1995) 1189–1193) and transgenic mice overexpressing IGF-II under the control of a more general promoter develop an elevated number and wide spectrum of tumor types (Rogler et al., *J. Biol. Chem.* 269 (1994) 13779–13784). One example among many for human tumors overexpressing IGF-I or IGF-II at very high frequency (>80%) are Small Cell Lung Carcinomas (Quinn et al., *J. Biol. Chem.* 271 (1996) 11477–11483). Signaling by the IGF system seems to be also required for the transforming activity of certain oncogenes. Fetal fibroblasts with a disruption of the IGF-1R gene cannot be transformed by the SV40 T antigen, activated Ha-ras, or a combination of both (Sell et al., *Proc. Natl. Acad. Sci. USA* 90 (1993) 11217–11221; Sell et al., *Mol. Cell. Biol.* 14 (1994) 3604–3612), and the E5 protein of the bovine papilloma virus is also no longer transforming (Morrione et al., *J. Virol.* 69 (1995) 5300–5303). Interference with the IGF/IGF-1R system was also shown to reverse the transformed phenotype and to inhibit tumor growth (Trojan et al., *Science* 259 (1993) 94–97; Kalebic et al., *Cancer Res.* 54 (1994) 5531–5534; Prager et al., Proc. Natl. Acad, Sci. USA 91 (1994) 2181–2185; Resnicoff et al., *Cancer Res.* 54 (1994) 2218–2222; Resnicoff et al., *Cancer Res.* 54 (1994) 4848–4850; Resnicoff et al., *Cancer Res.* 55 (1995) 2463–2469. For example, mice injected with rat prostate adenocarcinoma cells (PA-III) transfected with IGF-1R antisense cDNA (729 bp) develop tumors 90% smaller than controls or remained tumor-free after 60 days of observation (Burfeind et al., *Proc. Natl. Acad. Sci. USA* 93 (1996) 7263–7268). IGF-1R mediated protection against apoptosis is independent of de-novo gene expression and protein synthesis. Thus, IGF-1 likely exerts its anti-apoptotic function via the activation of preformed cytosolic mediators.

Some signaling substrates which bind to the IGF-1R (e.g. IRS-1, SHC, p85 P13 kinase etc., for details see below) have been described. However, none of these transducers is unique to the IGF-1R and thus could be exclusively responsible for the unique biological features of the IGF-1R compared to other receptor tyrosine kinase including the insulin receptor. This indicates that specific targets of the IGF-1R (or at least the IGF-receptor subfamily) might exist which trigger survival and counteract apoptosis and thus are prime pharmaceutical targets for anti-cancer therapy.

By using the yeast two-hybrid system it was shown that p85, the regulatory domain of phosphatidyl inositol 3 kinase (P13K), interacts with the IGF-1R (Lamothe, B., et al., *FEBS Lett.* 373 (1995) 51–55; Tartare-Decker, S., et al., *Endocrinology* 137 (1996) 1019–1024). However binding of p85 to many other receptor tyrosine kinases of virtually all families is also seen. Another binding partner of the IGF-1R defined by two-hybrid screening is SHC which binds also to other tyrosine kinases such as trk, met, EGF-R and the insulin receptor (Tartare-Deckert, S., et al., *J. Biol. Chem.* 270 (1995) 23456–23460). The insulin receptor substrate 1 (IRS-1) and insulin receptor substrate 2 (IRS-2) were also found to both interact with the IGF-1R as well as the insulin receptor (Tartare-Deckert, S., et al., *J. Biol. Chem.* 270 (1995) 23456–23460; He, W., et al., *J. Biol. Chem.* 271 (1996) 11641–11645; Dey, R. B., et al., *Mol. Endocrinol.* 10 (1996) 631–641). Grb 10 which interacts with the IGF-1R also shares many tyrosine kinases as binding partners, e.g. met, insulin receptor, kit and abl (Dey, R. B., et al., Mol. Endocrinol. 10 (1996) 631–641; Morrione, A., et al., *Cancer Res.* 56 (1996) 3165–3167). The phosphatase PTP1D (syp) shows also a very promiscuous binding capacity, i.e. binds to IGF-1R, insulin receptor, met and others (Rocchi, S., et al., *Endocrinology* 137 (1996) 4944–4952). More recently, mSH2-B and vav were described as binders of the IGF-1R, but interaction is also seen with other tyrosine kinases, e.g. mSH2-B also bind to ret and the insulin receptor (Wang, J., and Riedel, H., *J. Biol. Chem.* 273 (1998) 3136–3139). Taken together, the so far described IGF-1R binding proteins represent relatively unspecific targets for therapeutic approaches, or are in the case of the insulin receptor substrates (IRS-1, IRS-2) indispensable for insulin-driven activities.

SUMMARY OF THE INVENTION

The present invention relates to IGF-1 receptor interacting proteins (IIPs); nucleic acids coding therefor; and their use for diagnostics and therapeutics, especially in the field of cancer. In particular, the invention relates to the identification of said genes in mammalian cells, especially in malignant tumor cells; to gene therapy methods for inhibiting the interaction between IGF-1 receptor and IIPs; methods of screening for potential cancer therapy agents; and cell lines and animal models useful in screening for and evaluating potentially useful pharmaceutical agents that inhibit the interaction between IIPs; and IGF-1 receptor.

The present invention relates in particular to the cloning and characterization of the gene IIP-10 and the gene products thereof. Said gene products (polypeptides, mRNA) are especially characterized as having the ability to modulate the IGF-1 receptor signaling pathway. The function of the gene products according to the invention is therefore to modulate signal transduction of the IGF-1 receptor. Forced activation of IIPs therefore correlates with increased tumor cell proliferation, survival and escape of apoptosis.

It is an object of the invention to provide novel genes encoding binding proteins of IGF-1R as well as the corresponding polypeptides which modulate, preferably activate the IGF-1 receptor signaling pathway. It is envisioned that this invention provides a basis for new cancer therapies based on the modulation, preferably inhibition, of the interaction between IGF-1 R and IIPs.

DESCRIPTION OF THE FIGURES AND SEQUENCES

Figure 1B:
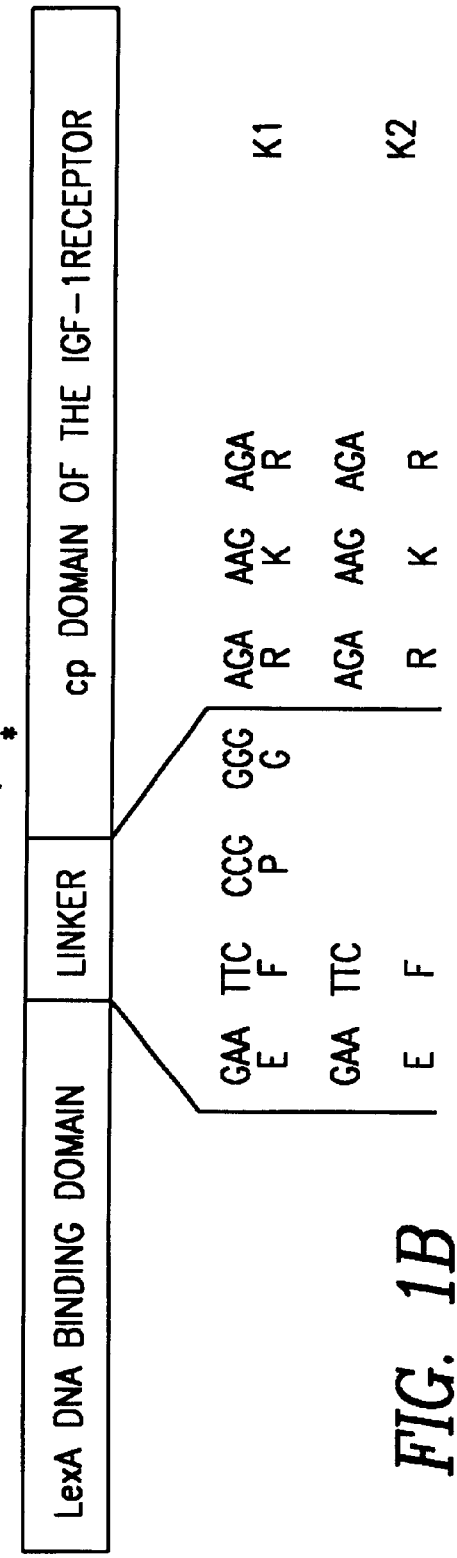
Figure 2A:
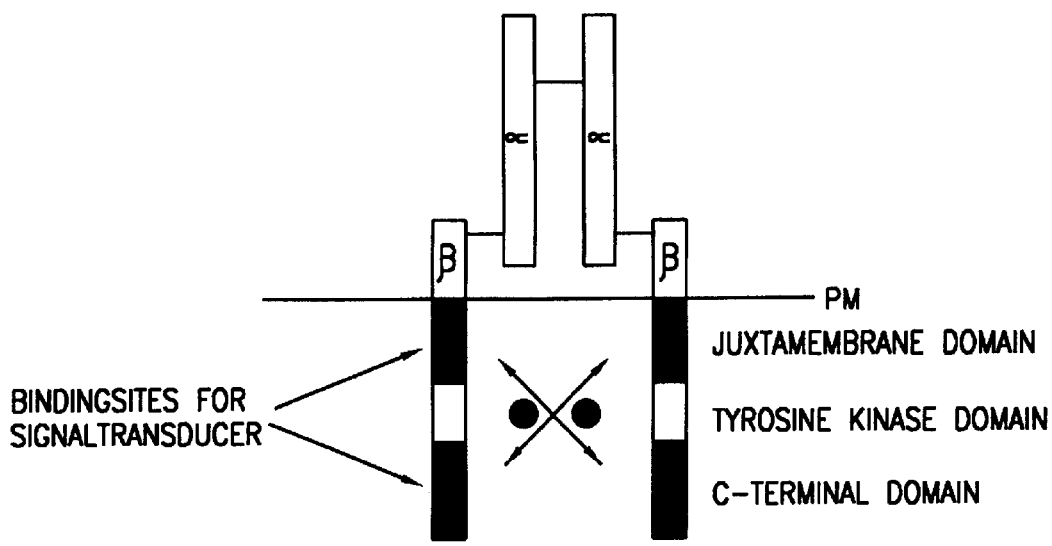
Figure 2B:
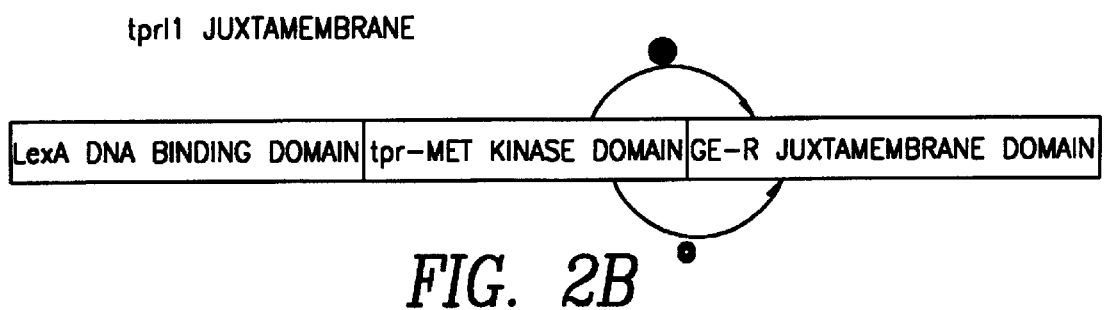
Figure 2C:
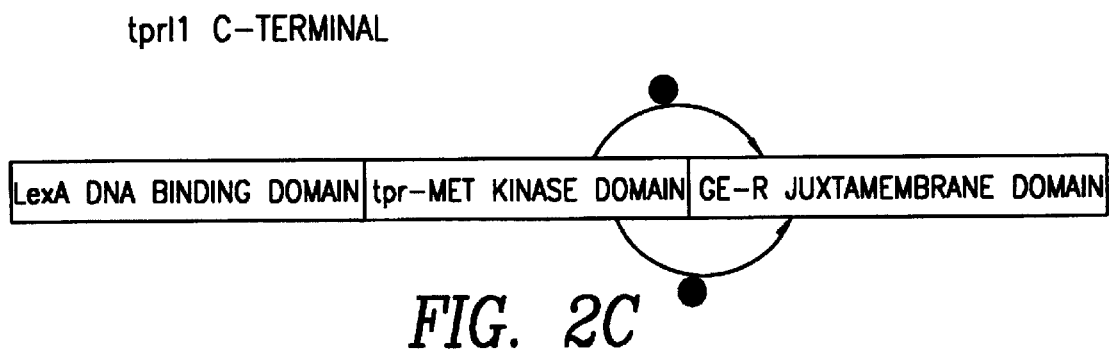

| | |
|---|---|
| Figure 1 | Domain structure of yeast two-hybrid baits which were used to screen cDNA libraries for cytoplasmic binding proteins of the IGF-1 receptor.<br>The LexA DNA binding domain was fused to the cytoplasmic (cp) domain (nt 2923 to 4154) of the wildtype IGF-1 receptor (a) or the kinase inactive mutant (K/A mutation at aa 1003) (b) (Ullrich, A., et al., EMBO J. 5 (1986) 2503–2512; Weidner, K. M., et al., Nature 384 (1996) 173–176). The nucleotide and amino acid sequence of two different linkers inserted between the LexA DNA-binding domain and the receptor domain are shown below. The I1 (wt IGF-1 receptor) and K1 (kinase inactive mutant IGF-1 receptor) constructs contain an additional proline and glycine compared to the 12 and K2 constructs. |
| Figure 2 | Modification of the yeast two-hybrid LexA/IGF-1 receptor bait construct.<br>a) Schematic illustration of cytoplasmic binding sites of the IGF-1 receptor. The α-subunits of the IGF-1 receptor are linked to the β-chains via disulfid bonds. The cytoplasmic part of the β-chain contains binding sites for substrates in the juxtamembrane and C-terminal domain.<br>b) Domain structure of the two-hybrid bait containing only the juxtamembrane IGF-1 receptor binding sites. The juxtamembrane domain of the IGF-1 receptor (nt 2923 to 3051) (Ullrich, A., et al., EMBO J. 5 (1986) 2503–2512) was fused to the kinase domain of tprmet (nt 3456 to 4229) (GenBank accession number: HSU19348).<br>c) Domain structure of the two-hybrid bait containing only the C-terminal IGF-1 receptor binding sites. The C-terminal domain of the IGF-1 receptor (nt 3823 to 4149) (Ullrich, A., et al., EMBO J. 5 (1986) 2503–2512) was fused to the kinase domain of tprmet (nt 3456 to 4229) (GenBank accession number: HSU19348). |
| Figure 3 | Isoforms of IIP-1.<br>a) Delineation of the cDNA sequences of IIP-1 and IIP-1 (p26). Nucleotides are numbered above. The potential translation initiation site within the IIP-1 cDNA is at position 63. The first ATG as potential translation initiation site in the alternative splice variant IIP-1 (p26) is at position 353. Both cDNAs contain a stop codon at position 1062.<br>b) Domain structure of IIP-1 and IIP-1 (p26). Amino acid positions are indicated above. In comparison to IIP-1 (p26) IIP- 1 contain additional 97 amino acids at the N-terminus. Both isoforms of IIP-1 contain a PDZ domain spanning a region between amino acids 129 and 213. |
| Figure 4 | Delineation of the IGF-1 receptor binding domain of IIP-1. Full-length IIP-1, its partial cDNA clones (IIP-1a and IIP-1b) and deletion mutants (IIP-1a/mul, IIP-1a/mu2, IIP-1a/mu3, IIP-1b/mul) were examined for interaction with the IGF-1 receptor in the yeast two-hybrid system. Yeast cells were cotransfected with a LexA IGF-1 receptor fusion construct and an activation plasmid coding for IIP-1 or the different IIP-1 mutants fused to the VP16 activation domain. Interaction between IIP-1 or its mutants and the IGF-1 receptor was analyzed by monitoring growth of yeast transfectants plated out on histidine deficient medium and incubated for 6 d at 30° C. (diameter of yeast colonies: +++,>1 mm in 2 d; ++,>1 mm in 4 d; +,>1 mm in 6 d; –, no detected growth). The PDZ domain can be defined as essential and sufficient for mediating the interaction with the IGF-1 receptor. Nucleotide positions with respect to full length IIP-1 are indicated above. |
| Figure 5 | Protein sequence motifs of IIP-10.<br>The amino acid sequence of IIP-10 was analyzed using the computer program "Motifs" (Wisconsin Package Version 10.0, Genetics Computer Group (GCG), Madison, Wisconsin) which looks for protein motifs by searching protein sequences for regular expression patterns described in the PROSITE Dictionary. |
| SEQ ID NO:1 | Nucleotide sequence of IIP-1 (cDNA). |
| SEQ ID NO:2 | Predicted amino acid sequence of IIP-1. |
| SEQ ID NO:3 | Nucleotide sequence of the IIP-6 partial cDNA clone. |
| SEQ ID NO:4 | Deduced amino acid sequence of the IIP-6 partial cDNA clone. Cysteine and histidine residues of the two $Cys_2His_2$ Zinc finger domains are amino acids 72, 75, 88, 92, 100, 103, 116, and 120. |
| SEQ ID NO:5 | Nucleotide sequence of IIP-10 (cDNA). |
| SEQ ID NO:6 | Deduced amino acid sequence of IIP-10. |
| SEQ ID NO:7 | Primer TIP2c-s. |
| SEQ ID NO:8 | Primer TIP2b-r. |
| SEQ ID NO:9 | Primer Hcthy-s. |
| SEQ ID NO:10 | Primer Hcthy-r. |

DETAILED DESCRIPTION OF THE INVENTION

The present invention relates to IGF-1 receptor interacting proteins (IIPs); nucleic acids coding therefor; and their use for diagnostics and therapeutics, especially in the field of cancer. The invention preferably comprises a nucleic acid encoding a protein (IIP-10) binding to IGF-1 receptor selected from the group comprising a) the nudeic acids shown in SEQ ID NO:5 or a nucleic acid sequence which is complementary thereto, b) nucleic acids which hybridize under stringent conditions with one of the nucleic acids from a) which encode a polypeptide showing at least 75% homology with the polypeptide of SEQ ID NO:6 or c) sequences that, due to the degeneracy of the genetic code, encode IIP-10 polypeptides having the amino acid sequence of the polypeptides encoded by the sequences of a) and b).

The cDNA of IIP-10 codes for a new protein of 226 amino acid with a calculated molecular weight of 25.697. IIP-10 is a lysine rich protein (11%). IIP-10 contains an N-glycosylation site, several N-myristoylation sites, Ck2 and PKC phosphorylation sites, one tyrosine kinase phosphorylation site and one putative nuclear localization signal (FIG. 5). The cDNA sequence of IIP-10 shows 65% homology to the cDNA sequence of the Gallus Gallus thymocyte protein cthy28kD (EMBL accession number: GG34350). The amino acid sequences of IIP-10 and cthy28kD show 70% identity. Nt 383 to nt 584 of the IIP-10 cDNA are 94% identical to a partial cDNA described in WO 95/14772 (human gene signature HUMGS06271; accession number T24253). By immunofluorescence, flag-tagged IIP-10 shows both a cytoplasmic and a nuclear localization in NIH3T3 cells overexpressing the IGF-1 receptor. Further yeast two-hybrid analysis revealed that IIP-10 interacts in a phosphorylation dependent manner with the IGF-1 receptor. IIP-10 does not interact with the insulin receptor. Deletion analysis of IIP-10 revealed that aa 19 to aa 226 are sufficient for binding to the IGF-1 receptor.

"Interaction" or "binding between IIP 10 and the IGF-1 receptor" means a specific binding of the IIP 10 polypeptide to the IGF-1 receptor but not to control proteins such as lamin in the yeast two hybrid system. Specific binding to the IGF-1 receptor can be demonstrated using glutathion-S-transferase (GST)-IIP fusion proteins expressed in bacteria and IGF-1 receptors expressed in mammalian cells. Furthermore, an association between a Flag tagged IIP-10 fusion protein (cf. Weidner, K. M. et al., Nature 384 (1996) 173–176) and the IGF-1 receptor can be monitored in mammalian cell systems. For this purpose eukaryotic expression vectors are used to transfect the respective cDNAs. Interaction between the proteins is visualized by coimmunoprecipitation experiments or subcellular localization studies using anti-Flag or anti-IGF-1 receptor antibodies.

Further provided by the invention are probes and primers for the genes according to the invention, as well as nucleic acids which encode antigenic determinants of the gene products according to the invention. Therefore, preferred embodiments include nudeic acids with preferably 10 to 50, or more preferably, 10 to 20 consecutive nucleotides out of the disclosed sequences.

The term "nucleic acid" denotes a polynucleotide which can be, for example, a DNA, RNA, or derivatized active DNA or RNA. DNA and mRNA molecules are preferred, however.

The term "hybridize under stringent conditions" means that two nucleic acid fragments are capable of hybridization to one another under standard hybridization conditions described in Sambrook et al., *Molecular Cloning: A laboratory manual* (1989) Cold Spring Harbor Laboratory Press, New York, USA.

More specifically, "stringent conditions" as used herein refers to hybridization in 5.0×SSC, 5×Denhardt, 7% SDS, 0.5 M phosphate buffer pH 7.0, 10% dextran sulfate and 100 $\mu$g/ml salmon sperm DNA at about 50° C.–68° C., followed by two washing steps with 1×SSC at 68° C. In addition, the temperature in the wash step can be increased from low stringency conditions at room temperatures, about 22° C., to high stringency conditions at about 68° C.

The invention further comprises recombinant expression vectors which are suitable for the expression of IIP-10, recombinant host cells transfected with such expression vectors, as well as a process for the recombinant production of a protein which is encoded by the IIP-10 gene.

The invention further comprises synthetic and recombinant polypeptides which are encoded by the nucleic acids according to the invention, and preferably encoded by the DNA sequence shown in SEQ ID NO:5 as well as peptidomimetics based thereon. Such peptidomimetics have a high affinity for cell membranes and are readily taken up by the cells. Peptidomimetics are preferably compounds derived from peptides and proteins, and are obtained by structural modification using unnatural amino acids, conformational restraints, isosterical placement, cyclization, etc. They are based preferably on 24 or fewer, preferably 20 or fewer, amino acids, a basis of approximately 12 amino acids being particularly preferred.

The polypeptides and peptidomimetics can be defined by their corresponding DNA sequences and by the amino acid sequences derived therefrom. The isolated IIP polypeptide can occur in natural allelic variations which differ from individual to individual. Such variations of the amino acids are usually amino acid substitutions. However, they may also be deletions, insertions or additions of amino acids to the total sequence leading to biologically active fragments. The IIP protein according to the invention—depending, both in respect of the extent and type, on the cell and cell type in which it is expressed—can be in glycosylated or non-glycosylated form. IIP-Polypeptides with tumoricidic and/or metastatic activity can be identified by a tumor progression assay using mammalian cells expressing said polypeptides and measuring the proliferation capacity and apoptosis in relation to mammalian cells not expressing said polypeptides.

"Polypeptide with IIP-10 activity or IIP-10" therefore means proteins with minor amino acid variations but with substantially the same activity as IIP-10. Substantially the same means that the activities are of the same biological properties and the polypeptides show at least 75% homology (identity) in amino acid sequences with IIP-10. More preferably, the amino acid sequences are at least 90% identical. Homology according to the invention can be determined with the aid of the computer programs Gap or BestFit (University of Wisconsin; Needleman and Wunsch, *J. Biol. Chem.* 48 (1970) 443–453; Smith and Waterman, Adv. Appl. Math. 2 (1981) 482–489).

Other IIPs according to, and used by, the invention are in particular:

IIP-1

Figures 3A, 3B:
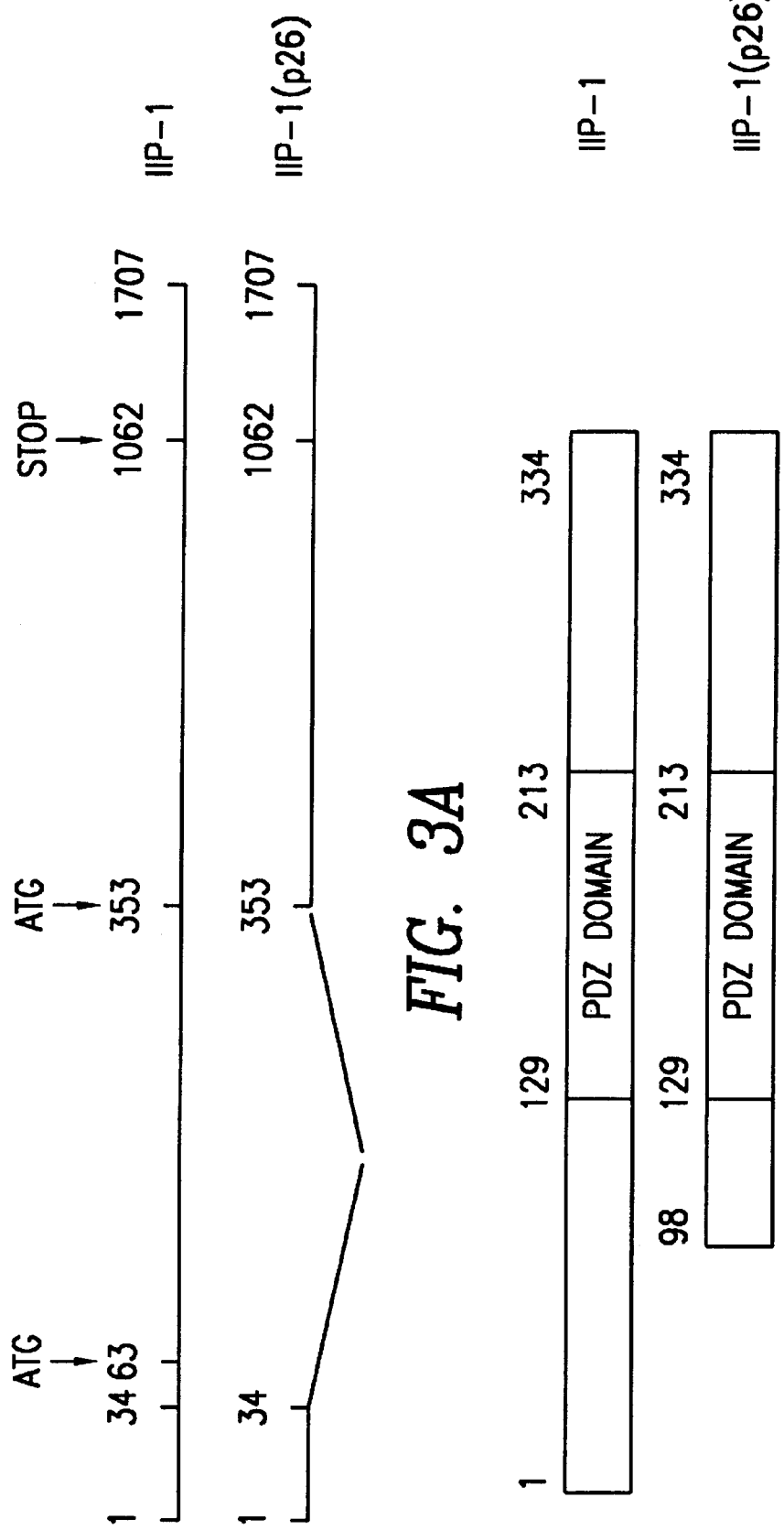

A cDNA encoding an IGF-1 receptor interacting protein which was named IIP-1 (SEQ ID NO:1) was isolated. The cDNA of IIP-1 codes for a new protein of 333 aa with a calculated molecular weight of 35,727. IIP-1 is a glycine rich protein (13%). IIP-I contains several N-myristoylation sites, PKC and Ck2 phosphorylation sites and two putative nuclear localization signals. A second isoform, IIP-1 (p26), of 236 aa in length with a calculated molecular weight of 26,071 was identified which was generated most likely by alternative splicing (FIG. 3). Both isoforms bind to the IGF-1 receptor.

cDNA sequences of IIP-1 have been reported previously (Database EMBL Nos. AF089818 and AF061263; DeVries, L., et al., *Proc. Natl. Acad. Sci.* USA 95 (1998) 12340–12345). Two overlapping cDNA clones (FIG. 4) were identified which show high homology to the human TIP-2 partial cDNA (GenBank accession number: AF028824) (Rousset, R., et al., *Oncogene* 16 (1998) 643–654) and were designated as IIP-1a and IIP-1b. The IIP-1a cDNA corresponds to nt 117 to 751 of TIP-2. The IIP-1b cDNA shows besides TIP-2 sequences (nt 1 to 106) additional 5' sequences which are homologous to sequence Y2H35 of WO 97/27296 (nt 25 to 158).

Figure 4:
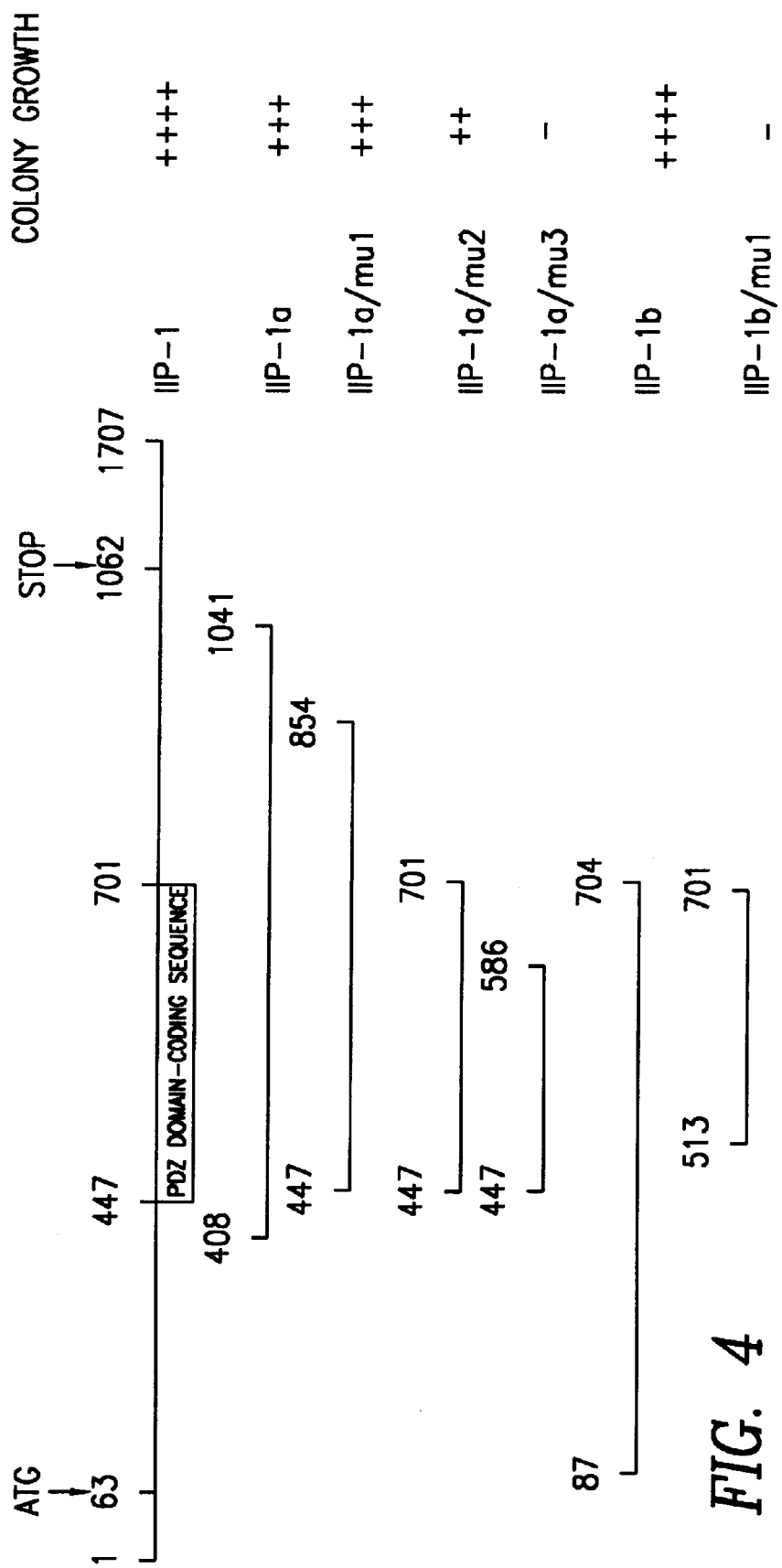

IIP-1a and IIP-1b both share the sequence coding for the PDZ domain of TIP-2 (nt 156 to 410) which is a known protein-protein interaction domain (Ponting, C. P., et al., *BioEssays* 19 (1997) 469–479). By deletion analysis the PDZ domain was determined as the essential and sufficient IGF-1 receptor binding domain of IIP-1 (FIG. 4).

Further yeast two-hybrid analysis revealed that binding of the IIP-1 protein to the IGF-1 receptor is specific for this receptor tyrosine kinase. No interaction was seen to the insulin receptor or Ros. Receptor tyrosine kinases of other families did not interact with IIP-I (e.g. Met, Ret, Kit, Fms, Neu, EGF receptor). Thus, IIP-1 most likely is the first interaction protein shown to be specific for the IGF-1 receptor tyrosine kinase. IIP-1 also binds to the kinase inactive mutant of the IGF-1 receptor.

IIP-2

IIP-2 was identified as a new binder of the cytoplasmic part of the IGF-1 receptor which corresponds to human APS (EMBL accession number: HSAB520). APS has been previously isolated in a yeast two-hybrid screen using the oncogenic c-kit kinase domain as bait (Yokouchi, M., et al., *Oncogene* 15 (1998) 7–15). IIP-2 interacts with the IGF-1 receptor in a kinase dependent manner. Binding of IIP-2 was also observed to other members of the insulin receptor family (insulin receptor, Ros), but not to an unrelated receptor tyrosine kinase (Met). The region of IIP-2 which was found to interact with the IGF-1 receptor corresponds to human APS (nt 1126 to 1674, EMBL Acc No. AB000520) contains the SH2 domain of APS (nt 1249 to 1545).

IIP-3

IIP-3 was isolated as a new IGF-1 receptor interacting protein and is identical to PSM (GenBank accession number: AF020526). PSM is known as a PH and SH2 domain containing signal transduction protein which binds to the activated insulin receptor (Riedel, H., et al., *J. Biochem.* 122 (1997) 1105–1113). A variant of PSM has also been described (Riedel, H., et al., *J. Biochem.* 122 (1997) 1105–1113). Binding of IIP-3 to the IGF-1 receptor is dependent on tyrosyl phosphorylation of the receptor.

A cDNA done corresponding to nt 1862 to 2184 of the variant form of PSM was identified. The isolated cDNA clone turned out to code for the IGF-1 receptor binding region. The SH2 domain of PSM (nt 1864 to 2148, EMBL Acc No. AF020526) is encoded by the sequence of the IIP-3 partial cDNA clone isolated.

IIP-4

IIP-4 was isolated as a new interacting protein of the cytoplasmic domain of the IGF-1 receptor. IIP-4 corresponds to p59fyn, a src-like tyrosine kinase (EMBL accession number: MMU70324 and human fyn EM_HUM1:HS66H14) (Cooke, M. P., and Perlmutter, R. M., *New Biol.* 1 (1989) 66–74). IIP-4 binds in a kinase dependent manner to the IGF-1 receptor and to several other receptor tyrosine kinases as to the insulin receptor and Met. The region of IIP-4 interacting with the IGF-1 receptor (nt 665 to 1044) contains the SH2 domain of p59fyn (EMBL Acc No. U70324).

IIP-5

IIP-5 was isolated as a new IGF-1 receptor interacting protein. IIP-5 shows a high homology to the zinc finger protein Zfp38 (EMBL accession number: MMZFPTA) and is at least 80% homologous to the corresponding human gene. Zfp-38 is known as a transcription factor (Chowdhury, K., et al., *Mech. Dev.* 39 (1992) 129–142). IIP-5 interacts exclusively with the activated and phosphorylated IGF-1 receptor, but not with a kinase inactive mutant. In addition to binding of IIP-5 to the IGF-1 receptor interaction of IIP-5 with receptor tyrosine kinases of the insulin receptor family (insulin receptor, Ros) was observed. IIP-5 does not bind to the more distantly related receptor tyrosine kinase Met.

One cDNA done binding to the IGF-1 receptor which codes for nt 756 to 1194 of Zfp38 (EMBL Acc No. MMZFPTA) and contains the first zinc finger (nt 1075 to 1158) was isolated. This domain is sufficient for binding to the activated IGF-1 receptor.

IIP-6

IIP-6 was identified as a new IGF-1 receptor interacting protein. IIP-6 shows weak similarity to the zinc finger domain of Zfp29 (EMBL accession number: MMZFP29). Zfp29 consists of a N-terminal transcriptional activation domain and 14 C-terminal $Cys^2His^2$ zinc fingers (Denny, P., and Ashworth, A., *Gene* 106 (1991) 221–227). Binding of IIP-6 to the IGF-1 receptor depends on phosphorylation of the IGF-1 receptor kinase. IIP-6 also binds to the insulin receptor, but does not interact with Met. The region of IIP-6 found to interact with the IGF-1 receptor (SEQ ID NO:3, SEQ ID NO:4) contains two zinc finger domains of the $Cys^2His^2$ type.

IIP-7

IIP-7 was isolated as a new IGF-1 receptor interacting protein which corresponds to Pax-3 (EMBL accession number: MMPAX3R and human Pax3 EM-HUM2:S69369). Pax-3 is known as a DNA-binding protein being expressed during early embryogenesis (Goulding, M. D., et al., *EMBO J.* 10 (1991) 1135–1147). IIP-7 binds in a phosphorylation dependent manner to the IGF-1 receptor. IIP-7 also interacts with the insulin receptor and Met. A partial IIP-7 cDNA clone turned out to code for the IGF-1 receptor binding domain of Pax3 (nt 815 to 1199, EMBL Acc No. MMPAX3R). This region contains the Pax-3 paired damain octapeptide (nt 853 to 876) and the paired-type homeodomain (nt 952 to 1134).

IIP-8

IIP-8 codes for the full-length cDNA of Grb7 (EMBL accession number: MMGRB7P, human Grb7 EM_HUM1:AB008789). Grb7, a PH domain and a SH3 domain containg signal transduction protein, was first published as an EGF receptor-binding protein (Margolis, B. L., et al., *Proc. Natl. Acad. Sci.* USA 89 (1992) 8894–8898). IIP-8 does not interact with the kinase inactive mutant of the IGF-1 receptor. Binding of IIP-8 to several other receptor tyrosine kinases (e.g. insulin receptor, Ros and Met) was also observed.

IIP-9

IIP-9 was identified as a new IGF-1 receptor interaction protein. IIP-9 is identical to nck-beta (EMBL Acc No. AF043260). Nck is a cytoplasmic signal transduction protein consisting of SH2 and SH3 domains (Lehmann, J. M., et al., *Nucleic Acids Res.* 18 (1990) 1048). IIP-9 interacts with the IGF-1 receptor in a phosphorylation dependent manner. nck binds to the juxtamembrane region of the IGF-1 receptor. Apart from binding of IIP-9 to the IGF-1 receptor, interaction with the insulin receptor but not with Ros or Met was seen.

A preferred object of the invention are polypeptides that are homologous, and more preferably, polypeptides that are substantially identical to the polypeptides of SEQ ID NO:6 (IIP-10). Homology can be examined by using the FastA algorithm described by Pearson, W. R., Methods in Enzymology 183 (1990) 63–68, Academic Press, San Diego, U.S. By "substantially identical" is meant an amino acid sequence which differs only by conservative amino acid substitutions, for example substitutions of one amino acid for another of the same class (e.g. valine for glycine, arginine for lysine, etc.) or by one or more non-conservative amino acid substitution, deletions or insertions located at positions of the amino acid sequence which do not destroy the biological function of the polypeptide. This includes substitution of alternative covalent peptide bonds in the polypeptide. By "polypeptide" is meant any chain of amino acids regardless of length or posttranslational modification (e.g., glycosylation or phosphorylation) and can be used interchangeably with the term "protein".

According to the invention by "biologically active fragment" is meant a fragment which can exert a physiological effect of the full-length naturally-occurring protein (e.g., binding to its biological substrate, causing an antigenic response, etc.).

The invention also features fragments of the polypeptide according to the invention which are antigenic. The term "antigenic" as used herein refers to fragments of the protein which can induce a specific immunogenic response, e.g. an immunogenic response which yields antibodies which specifically bind to the protein according to the invention. The fragments are preferably at least 8 amino acids, and preferably up to 25 amino acids, in length. In one preferred embodiment, the fragments include the domain which is responsible for the binding of the IIPs to the IGF-1 receptor (i.e., the PDZ domain of IIP-1. By "domain" is meant the region of amino acids in a protein directly involved in the interaction with its binding partner. PDZ domains are approximately 90-residue repeats found in a number of proteins implicated in ion-, channel and receptor clustering and the linking of receptors to effector enzymes. Such PDZ are described in general by Cabral, J. H., et al., Nature 382 (1996) 649–652.

The invention further comprises a method for producing a protein according to the invention whose expression or activation is correlated with tumor proliferation, by expressing an exogenous DNA in prokaryotic or eukaryotic host cells and isolation of the desired protein or expressing said exogenous DNA in vivo for pharmaceutical means, wherein the protein is coded preferably by a DNA sequence coding for IIP-10, preferably the DNA sequence shown in SEQ ID NO:5.

The polypeptides according to the invention can also be produced by recombinant means, or synthetically. Non-glycosylated IIP-10 polypeptide is obtained when it is produced recombinantly in prokaryotes. With the aid of the nucleic acid sequences provided by the invention it is possible to search for the IIP-10 gene or its variants in genomes of any desired cells (e.g. apart from human cells, also in cells of other mammals), to identify these and to isolate the desired gene coding for the IIP-10 protein. Such processes and suitable hybridization conditions (see also above, "stringent conditions") are known to a person skilled in the art and are described, for example, by Sambrook et al., *Molecular Cloning: A laboratory manual* (1989) Cold Spring Harbor Laboratory Press, New York, USA, and Hames, B. D., Higgins, S. G., *Nucleic acid hybridisation—a practical approach* (1985) IRL Press, Oxford, England. In this case the standard protocols described in these publications are usually used for the experiments.

The use of recombinant DNA technology enables the production of numerous active IIP-10 derivatives. Such derivatives can, for example, be modified in individual or several amino acids by substitution, deletion or addition. The derivatization can, for example, be carried out by means of site directed mutagenesis. Such variations can be easily carried out by a person skilled in the art (J. Sambrook, B. D. Hames, loc. cit.). It merely has to be ensured by means of the below-mentioned tumor cell growth inhibition assay that the characteristic properties of IIP-10 are preserved.

With the aid of such nucleic acids coding for an IIP-10 protein, the protein according to the invention can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as, e.g., *E. coli* as a prokaryotic host cell or *Saccharomyces cerevisiae,* teratocarcinoma cell line PA-1 sc 9117 (Büittner et al., *Mol. Cell. Biol.* 11 (1991) 3573–3583), insect cells, CHO or COS cells as eukaryotic host cells and the transformed or transduced host cells are cultured under conditions which allow expression of the heterologous gene. The isolation of the protein can be carried out according to known methods from the host cell or from the culture supernatant of the host cell. Such methods are described for example by Ausubel I., Frederick M., *Current Protocols in Mol. Biol.* (1992), John Wiley and Sons, New York. Also in vitro reactivation of the protein may be necessary if it is not found in soluble form in the cell culture.

The invention therefore in addition concerns a IIP polypeptide which is a product of prokaryotic or eukaryotic expression of an exogenous DNA.

The protein can be isolated from the cells or the culture supernatant and purified by chromatographic means, preferably by ion exchange chromatography, affinity chromatography and/or reverse phase HPLC.

IIP-10 can be purified after recombinant production by affinity chromatography using known protein purification techniques, including immunoprecipitation, gel filtration, ion exchange chromatography, chromatofocussing, isoelectric focussing, selective precipitation, electrophoresis, or the like.

Diagnostic Methods

The invention further comprises a method for detecting a nudeic acid molecule encoding an IIP-gene, comprising incubating a sample (e.g., body fluids such as blood, cell lysates) with a nucleic acid molecule according to the invention and determining hybridization under stringent conditions of said nucleic acid molecule to a target nucleic acid molecule for determination of presence of a nucleic acid molecule which is said IIP gene and therefore a method for the identification of IGF-1R activation or inhibition in mammalian cells or body fluids.

Therefore the invention also includes a method for the detection of the proliferation potential of a tumor cell comprising a) incubating a sample of body fluid of a patient suffering from cancer, a sample of cancer cells, or a sample of a cell extract or a cell culture supernatant of said cancer cells, whereby said sample contains nucleic acids with a nucleic acid probe which is selected from the group consisting of
  (i) the nucleic acids shown in SEQ ID NOS:1, 3 or 5 or a nucleic acid which is complementary thereto and
  (ii) nudeic acids which hybridize under stringent conditions with one of the nucleic acids from (i) and b) detecting hybridization by means of a further binding partner of the nudeic acid of the sample and/or the nucleic acid probe or by X-ray radiography.

Hybridization between the probe and nucleic acids from the sample indicates the presence of the RNA of such proteins. Such methods are known to a person skilled in the art and are described, for example, in WO 89/06698, EP-A 0 200 362, U.S. Pat. No. 2,915,082, EP-A 0 063 879, EP-A 0 173 251, EP-A 0 128 018.

In a preferred embodiment of the invention the coding nucleic acid of the sample is amplified before the test, for example by means of the known PCR technique. Usually a derivatized (labeled) nucleic acid probe is used within the framework of nucleic acid diagnostics. This probe is contacted with a denatured DNA or RNA from the sample which is bound to a carrier and in this process the temperature, ionic strength, pH and other buffer conditions are selected—depending on the length and composition of the nucleic acid probe and the resulting melting temperature of the expected hybrid—such that the labeled DNA or RNA can bind to homologous DNA or RNA (hybridization see also Wahl, G. M., et al., *Proc. Natl. Acad. Sci.* USA 76 (1979) 3683–3687). Suitable carriers are membranes or carrier materials based on nitrocellulose (e.g., Schleicher and Schüll, BA 85, Amersham Hybond, C.), strengthened or bound nitrocellulose in powder form or nylon membranes derivatized with various functional groups (e.g., nitro groups) (e.g., Schleicher and Schüll, Nytran; NEN, Gene Screen; Amersham Hybond M.; Pall Biodyne).

Hybridizing DNA or RNA is then detected by incubating the carrier with an antibody or antibody fragment after thorough washing and saturation to prevent unspecific binding. The antibody or the antibody fragment is directed towards the substance incorporated during derivatization into the nucleic acid probe. The antibody is in turn labeled. However, it is also possible to use a directly labeled DNA. After incubation with the antibodies it is washed again in order to only detect specifically bound antibody conjugates. The determination is then carried out according to known methods by means of the label on the antibody or the antibody fragment.

The detection of the expression can be carried out for example as:

in situ hybridization with fixed whole cells, with fixed tissue smears and isolated metaphase chromosomes, colony hybridization (cells) and plaque hybridization (phages and viruses), Southern hybridization (DNA detection), Northern hybridization (RNA detection), serum analysis (e.g., cell type analysis of cells in the serum by slot-blot analysis), after amplification (e.g., PCR technique).

Preferably the nucleic acid probe is incubated with the nucleic acid of the sample and the hybridization is detected optionally by means of a further binding partner for the nucleic acid of the sample and/or the nucleic acid probe.

The nucleic acids according to the invention are hence valuable prognostic markers in the diagnosis of the metastatic and progression potential of tumor cells of a patient.

Screening for Antagonists and Agonists of IIPs or Inhibitors

According to the invention antagonists of IIP-10 or inhibitors for the expression of IIP (e.g., antisense nucleic acids) can be used to inhibit tumor progression and cause massive apoptosis of tumor cells in vivo, preferably by somatic gene therapy.

Therefore, the present invention also relates to methods of screening for potential therapeutics for cancer, diabetes, neurodegenerative disorders, bone diseases, to methods of treatment for disease and to cell lines and animal models useful in screening for and evaluating potentially useful therapies for such disease. Therefore another object of the invention are methods for identifying compounds which have utility in the treatment of the afore-mentioned and related disorders. These methods include methods for modulating the expression of the polypeptides according to the invention, methods for identifying compounds which can selectively bind to the proteins according to the invention and methods of identifying compounds which can modulate the activity of said polypeptides. These methods may be conducted in vitro and in vivo and may employ the transformed cell lines and transgenic animal models of the invention.

An antagonist of IIPs or an inhibitor of IIP is defined as a substance or compound which inhibits the interaction between IGF-1R and IIP, preferably IIP-10. Therefore the biological activity of IGF-1R decreases in the presence of such a compound. In general, screening procedures for IIP antagonists involve contacting candidate substances with IIP-bearing host cells under conditions favorable for binding and measuring the extent of decreasing receptor mediated signaling (in the case of an antagonist). Such an antagonist is useful as a pharmaceutical agent for use in tumor therapy. For the treatment of diabetes, neural diseases, or bone diseases, stimulation of the signaling pathway is required, i.e., screening for agonists is useful.

IIP activation may be measured in several ways. Typically, the activation is apparent by a change in cell physiology such as an increase or decrease in growth rate or by a change in the differentiation state or by a change in cell metabolism which can be detected in standard cell assays, for example MTT or XTT assays (Roche Diagnostics GmbH, DE).

The nudeic acids and proteins according to the invention could therefore also be used to identify and design drugs which interfere with the interaction of IGF-1R and IIPs. For instance, a drug that interacts with one of the proteins could preferentially bind it instead of allowing binding its natural counterpart. Any drug which could bind to the IGF-1 receptor and, thereby, prevent binding of an IIP or, vice versa, bind to an IIP and, thereby, prevent binding of the IGF-1 receptor. In both cases, signal transduction of the IGF-1 receptor system would be modulated (preferably inhibited). Screening drugs for this facility occurs by establishing a competitive assay (assay standard in the art) between the test compound and interaction of IIP and the IGF-1 receptor and using purified protein or fragments with the same properties as the binding partners.

The protein according to the invention is suitable for use in an assay procedure for the identification of compounds which modulate the activity of the proteins according to the invention. Modulating the activity as described herein includes the inhibition or activation of the protein and includes directly or indirectly affecting the normal regulation of said protein activity. Compounds which modulate the protein activity include agonists, antagonists and compounds which directly or indirectly affect the regulation of the activity of the protein according to the invention. The protein according to the invention may be obtained from both native and recombinant sources for use in an assay procedure to identify modulators. In general, an assay procedure to identify modulators will contain the IGF receptor, a protein of the present invention, and a test compound or sample which contains a putative modulator of said protein activity. The test compounds or samples may be tested directly on, for example, purified protein of the invention, whether native or recombinant, subcellular fractions of cells producing said protein, whether native or recombinant, and/or whole cells expressing said protein, whether native or recombinant. The test compound or sample may be added to the protein according to the invention in the presence or absence of known modulators of said protein. The modulating activity of the test compound or sample may be determined by, for example, analyzing the ability of the test compound or sample to bind to said protein, activate said protein, inhibit its activity, inhibit or enhance the binding of other compounds to said protein, modifying receptor regulation or modifying intracellular activity.

The identification of modulators of the protein activity are useful in treating disease states involving the protein activity. Other compounds may be useful for stimulating or inhibiting the activity of the protein according to the invention. Such compounds could be of use in the treatment of diseases in which activation or inactivation of the protein according to the invention results in either cellular proliferation, cell death, non-proliferation, induction of cellular neoplastic transformations, or metastatic tumor growth and hence could be used in the prevention and/or treatment of cancers such as, for example, prostate and breast cancer. The isolation and purification of a DNA molecule encoding the protein according to the invention would be useful for establishing the tissue distribution of said protein as well as establishing a process for identifying compounds which modulate the activity of said protein and/or its expression.

Therefore a further embodiment of the invention is a method for screening a compound that inhibits the interaction between IGF-1R and IIP-1, IIP-2, IIP3, IIP4, IIP5, IIP6, IIP7, IIP8, IIP9 or IIP-10, comprising a) combining IGF-1R and the IIP polypeptide with a solution containing a candidate compound such that the IGF-1R and the IIP polypeptide are capable of forming a complex and b) determining the amount of complex relative to the predetermined level of binding in the absence of said candidate compound and therefrom evaluating the ability of said candidate compound to inhibit binding of IGF-1R to the IIP polypeptide.

Such a screening assay is preferably performed as an ELISA assay whereby IGF-1R or the IIP-polypeptide preferably IIP-1 or IIP-10, is bound on a solid phase.

A further embodiment of the invention is a method for the production of a therapeutic agent for the treatment of carcinomas in a patient comprising combining a therapeutically effective amount of a compound which inhibits the interaction between IGF-1R and IIP in biochemical and/or cellular assays to an extent of at least 50%. Biochemical assays are preferably ELISA-based assays or homogeneous assays. In the case of the ELISA system antibodies specific for the two binding partners are used for detection of the complexes. In the case of the homogenous assay at least one binding partner is labeled with fluorophores which allows analysis of the complexes. Cellular assays are preferably assays whereby tumor cells or cells transfected with expression constructs of the IGF-1R and the respective binding proteins are treated with or without drugs and complex formation between the two components is then analyzed using standard cell assays.

A preferred embodiment of the invention is a method for the production of a therapeutic agent for the treatment of carcinomas in a patient comprising combining a pharmaceutically acceptable carrier with a therapeutically effective amount of a compound which inhibits the interaction between IGF-1R and an IIP-polypeptide, preferably IIP-1 or IIP-10, in a cellular assay, whereby in said cellular assay tumor cells or cells transfected with expression constructs of IGF-1R and of the respective IIP are treated with said compound, and complex formation between IGF-1R and said respective IIP is analyzed, and the extent of said complex formation in the case of inhibition does not exceed 50% referred to 100% for complex formation without said compound in said same cellular assay.

A further embodiment of the invention is a method of treating a patient suffering from a carcinoma with a therapeutically effective amount of a compound which inhibits the interaction between IGF-1R and the IIP-polypeptide, preferably IIP-1 or IIP-10, in a cellular assay, whereby in said cellular assay tumor cells or cells transfected with expression constructs of IGF-1R and of the respective IIP are treated with said compound, and complex formation between IGF-1R and said respective IIP is analyzed, and the extent of said complex formation in the case of inhibition does not exceed 50% referred to 100% for complex formation without said compound in said same cellular assay.

A further embodiment of the invention is an antibody against IIP-1 or IIP-10 according to the invention.

Antibodies were generated from the human, mouse, or rat polypeptides. Antibodies specifically recognizing IIP-1 or IIP-10 are encompassed by the invention. Such antibodies are raised using standard immunological techniques. Antibodies may be polyclonal or monoclonal or may be produced recombinantly such as for a humanized antibody. An antibody fragment which retains the ability to interact with IIP-1 or IIP-10 is also provided. Such a fragment can be produced by proteolytic cleavage of a full-length antibody or produced by recombinant DNA procedures. Antibodies of the invention are useful in diagnostic and therapeutic applications. They are used to detect and quantitate IIP-1 or IIP-10 in biological samples, particularly tissue samples and body fluids. They are also used to modulate the activity of IIP-1 or IIP-10 by acting as an agonist or an antagonist.

The following examples, references, sequence listing and drawing are provided to aid the understanding of the present invention, the true scope of which is set forth in the appended claims. It is understood that modifications can be made in the procedures set forth without departing from the spirit of the invention.

EXAMPLES

Example 1

Isolation and Characterization of IGF-1R Binding Proteins

The yeast two-hybrid system (Fields, S., and Song, O., *Nature* 340 (1989) 245–246) was used to isolate unknown cytosolic IGF-1 receptor binding proteins. For screening a modified version of the yeast two-hybrid system was used which allows interchain tyrosylphosphorylation of the receptors in yeast.

The yeast two-hybrid bait plasmid (BTM116-cpIGF-1 receptor) was constructed by fusing the cytoplasmic domain of the β-subunit of the IGF-1 receptor (nt 2923 to 4154) (Ullrich, A., et al., *EMBO J.* 5 (1986) 2503–2512) to the LexA DNA-binding domain which forms dimers and mimics the situation of the activated wildtype receptor (cf. Weidner, M., et al., *Nature* 384 (1996) 173–176). By introducing a proline-glycine spacer between the LexA DNA-binding domain and the receptor domain the ability of the bait to bind known substrates of the IGF-1 receptor was remarkably increased in comparision to other spacer amino acids (FIG. 1).

Alternatively a bait was constructed containing only the juxtamembrane or C-terminal region of the IGF-1 receptor (nt 2923 to 3051 or nt 3823 to 4146) (Ullrich, A., et al., *EMBO J.* 5 (1986) 2503–2512) fused to the kinase domain of an unrelated, very potential receptor tyrosine kinase. Here the kinase domain of tpr met (nt 3456 to 4229) (GenBank accession number: HSU19348) (FIG. 2) was used. In this way it is possible to delineate the region of the IGF-1 receptor which mediates binding to downstream effectors.

The IGF-1 receptor bait plasmid was used to screen activation domain cDNA libraries (e.g. VP16- or Gal4 based activation domain) (cf. Weidner, M., et al., *Nature* 384 (1996) 173–176). The bait and prey plasmids were co-transfected into Saccharomyces cerevisiae strain L40 containing a HIS3 and lacZ reporter gene. Library plasmids were isolated from yeast colonies growing on histidine deficient medium, were sequenced and reintroduced into yeast strain L40. By co-transfecting experiments with different test baits, i.e. BTM116 plasmids coding for a kinase inactive mutant of the IGF-1 receptor (L1033A) or the cytoplasmic domain of receptor tyrosine kinases of the insulin receptor family (insulin receptor, Ros) and of unrelated receptor tyrosine kinase families (Met, EGF receptor, Kit, Fms, Neu) the specificity of the putative bait-prey interactions was evaluated. Several cDNAs were identified which code for previously unknown IGF-1 receptor interacting proteins (IIPs). In addition binding domains of known substrates of the IGF-1 receptor such as the C-terminal SH2 domain of p85PI3K and the SH2 domain of Grb10 were found. The results are shown in Table 1.

TABLE 1

| IIP | wt IGF-1R | mu IGF-1R | IR | Ros | Met |
| --- | --- | --- | --- | --- | --- |
| IIP-1 | + | + | − | − | − |
| IIP-2 | + | − | + | + | − |
| IIP-3 | + | − | + | + | + |
| IIP-4 | + | − | + | nd | + |

TABLE 1-continued

| IIP | wt IGF-1R | mu IGF-1R | IR | Ros | Met |
| --- | --- | --- | --- | --- | --- |
| IIP-5 | + | − | + | + | − |
| IIP-6 | + | − | + | nd | − |
| IIP-7 | + | − | + | nd | + |
| IIP-8 | + | − | + | + | + |
| IIP-9 | + | − | + | − | − |
| IIP-10 | + | − | − | nd | nd |

Delineation of the binding specificity of the IIPs with respect to different receptor tyrosine kinases tested in the yeast two-hybrid system. Yeast cells were cotransfected with a LexA fusion construct coding for the different receptor tyrosine kinases and an activation plasmid coding for the different IIPs fused to the VP16 activation domain. Interaction between the IIPs and the different receptor tyrosine kinases was analyzed by monitoring growth of yeast transfectants plated out on histidine deficient medium and incubated for 3d at 30° C. (wt IGF-1R, kinase active IGF-1 receptor; mu IGF-1R, kinase inactive mutant IGF-1 receptor; IR, insulin receptor; Ros, Ros receptor tyrosine kinase; Met, Met receptor tyrosine kinase; +, growth of yeast transfectants within 3 days larger than 1 mm in diameter; −, no detected growth; nd, not determined).

Example 2

Assay Systems

A) In-vitro/Biochemical Assays

ELISA-based Assay/Homogenous Assay

IGF-1R and the binding proteins (IIPs) are expressed with or without Tag-epitopes in E.coli or eucaryotic cells and purified to homogeneity. Interaction of IGF-1R and the respective binding proteins are analyzed in the presence or absence of drugs. Compounds which either inhibit or promote binding of IGF-1R and the respective binding proteins are selected. In the case of the ELISA system antibodies specific for the two binding partners are used for detection of the complexes. In the case of the homogenous assay at least one binding partner is labeled with fluorophores which allows analysis of the complexes. Alternatively, anti-Tag-antibodies are used to monitor interaction.

B) Cellular Assays

Tumor cells or cells transfected with expression constructs of the IGF-1R and the respective binding proteins are treated with or without drugs and complex formation between the two components is then analyzed using standard assays.

Example 3 cDNA Cloning of IIP-1 and IIP-10 (and RT-PCR-assay)

The nucleotide sequence of full length IIP-1 was determined by sequencing of the partial cDNA clones of IIP-1 and (IIP-1a, IIP-1b) and by using database information (ESTs). cDNA cloning of full length IIP-1 was performed by RT PCR on total RNA isolated from a MCF7$_{ADR}$breast cell line. PT PCR with two oligonucleotide primers: TIP2c-s (SEQ ID NO:7) and TIP2b-r (SEQ ID NO:8) resulted in amplification of two DNA fragments of 1.0 kb (IIP-1) and 0.7 kb (IIP-1(p26)).

The nucleotide sequence of full length IIP-10 was determined by sequencing of the partial cDNA done of IIP-10 and by using database information (ESTs). cDNA cloning of IIP-10 was performed on total RNA isolated from the colon cancer cell line SW480.RT PCR with two oligonucleotide primers: Hcthy-s (SEQ ID NO:9) and Hcthy-r (SEQ ID NO:10) resulted in amplification of a cDNA fragment of 676bp (IIP-10).

DNA sequencing was performed using the dideoxynucleotide chain termination method on an ABI 373A sequencer using the Ampli Taq® FS Dideoxyterminator kit (Perkin Elmer, Foster City, Calif.). Comparison of the cDNA and deduced protein sequences was performed using Advanced Blast Search (Altschul, S. F., et al., J. Mol. Biol. 215 (190) 403–410; Altschul, S. F., et al., Nucleic Acids Res. 25 (1997) 3389–3402).

Example 4

Western Blot Analysis of IIP-1 and IIP-10

Total cell lysates were prepared in a buffer containing 50 mM Tris pH 8.0, 150 mM NaCl, 1% NP40, 0.5 % deoxycholic acid, 0.1 % SDS, and 1 mM EDTA and cleared by centrifugation for 15 min at 4° C. The protein concentration of the supernatants was measured using the Micro BCA Protein Assay kit (Pierce Chemical Co., Rockford, Ill.) according to the manufacturer's manual. IGF-1 receptors were immunoprecipitated using anti-IGF-1 receptor antibodies (Santa Cruz). Proteins were fractionated by SDS-PAGE and electrophoretically transferred to nitrocellulose filters. Nitrocellulose filters were preincubated with 10% (w/v) fat-free milk powder in 20 mM Tris pH 7.5, 150 mM NaCl, 0.2% Tween-20. Binding of a mouse monoclonal antibody directed against the flag epitope was detected by horseradish peroxidase-labeled goat-anti-mouse IgG antiserum (Biorad, Munich, DE) and visualized using an enhanced chemoluminescence detection system, ECL™ (Amersham, Braunschweig, Del.).

Example 5

Overexpression of IIP-1 to IIP-10 in Mammalian Cells by Liposome-mediated Transfection The cDNAs for IIP-1 to -10 were cloned into the NotI site of pBATflag or pcDNA3flag (Weidner, K. M., et al., Nature 384 (1996) 173–176); Behrens, J., et al., Nature 382 (1996) 638–642); Behrens, J., et al., Science 280 (1998) 596–599). NIH3T3 cells or other recipient cells were transfected with pcDNAflagIIP-1 to -10 or alternatively with pBATflag IIP-1 to -10 using FuGENE6 (Roche Biochemicals) as transfection agent. Cells were selected in 0.4 mg/ml G418. Single clones were picked and analzyed for expression of IIP-1 to -10 and functionally characterized with respect to proliferation.

Northern Blot Analysis

Human and murine mRNA multiple tissue Northern blots were purchased from Clontech (Palo Alto, Calif., U.S.). A cDNA probe spanning IIP-10 nt343-nt676 of the coding region was labeled with DIG-dUTP using the PCR DIG Labeling Mix (Roche Diagnostics GmbH, DE). A digoxygenin labeled actin RNA probe was purchased from Roche Diagnostics GmbH, DE. Hybridization was performed using the DIG EasyHyb hybridization solution (Roche Diagnostics GmbH, DE). IIP-10 mRNA was detected with DIG-specific antibodies conjugated to alkaline phosphatase and the CSPD substrate (Roche Diagnostics GmbH, DE).

Example 6

Detection of mRNA in Cancer Cells

In order to detect whether proteins are expressed in cancer cells which are coded by nucleic acids which hybridize with SEQ ID NO:1 or SEQ ID NO:5 or the complementary sequence and consequently whether mRNA is present, it is possible on the one hand to carry out the established methods of nucleic acid hybridization such as Northern hybridization, in-situ hybridization, dot or slot hybridization and diagnostic techniques derived therefrom (Sambrook et al., *Molecular Cloning: A laboratory manual* (1989) Cold Spring Harbor Laboratory Press, New York, USA; Hames, B. D., Higgins, S. G., Nucleic acid hybridisation—a practical approach (1985) IRL Press, Oxford, England; WO 89/06698; EP-A 0 200 362; EP-A 0 063 879; EP-A 0 173 251; EP-A 0 128 018). On the other hand it is possible to use methods from the diverse repertoire of amplification techniques using specific primers (*PCR Protocols—A Guide to Methods and Applications* (1990), publ. M. A. Innis, D. H. Gelfand, J. J. Sninsky, T. J. White, Academic Press Inc.; *PCR—A Practical Approach* (1991), publ. M. J. McPherson, P. Quirke, G. R. Taylor, IRL Press).

The RNA for this is isolated from the cancer tissue by the method of Chomczynski and Sacchi, *Anal. Biochem.* 162 (1987) 156–159.20 µg total RNA was separated on a 1.2% agarose formaldehyde gel and transferred onto nylon membranes (Amersham, Braunschweig, DE) by standard methods (Sambrook et al., *Molecular Cloning: A laboratory manual* (1989) Cold Spring Harbor Laboratory Press, New York, USA. The DNA sequence SEQ ID NO:1 or SEQ ID NO:5 was radioactively labeled as probes (Feinberg, A. P., and Vogelstein, B., *Anal. Biochem.* 137 (1984) 266–267). The hybridization was carried out at 68° C. in 5×SSC, 5×Denhardt, 7% SDS/0.5 M phosphate buffer pH 7.0, 10% dextran sulfate and 100 µg/ml salmon sperm DNA. Subsequently the membranes were washed twice for one hour each time in 1×SSC at 68° C. and then exposed to X-ray film.

Example 7

Procedure for Identification of Modulators of the Activity of the Protein According to the Invention The expression vector of Example 5 (either for IIP-1 or IIP-10 10 µg/10⁶ cells) is transferred into NIH 3T3 cells by standard methods known in the art (Sambrook et al.). Cells which have taken up the vector are identified by their ability to grow in the presence of the selection or under selective conditions (0.4 mg/ml G418). Cells which express DNA encoding IIP produce RNA which is detected by Northern blot analysis as described in Example 5. Alternatively, cells expressing the protein are identified by identification of the protein by Western blot analysis using the antibodies described in Example 4. Cells which express the protein from the expression vector will display an altered morphology and/or enhanced growth properties.

Cells which express the protein and display one or more of the altered properties described above are cultured with and without a putative modulator compound. By screening of chemical and natural libraries, such compounds can be identified using high throughput cellular assays monitoring cell growth (cell proliferation assays using as chromogenic substrates the tetrazolium salts WST-1, MTT, or XTT, or a cell death detection ELISA using bromodesoxyuridine (BrdU); cf. Boehringer Mannheim GmbH, Apoptosis and Cell Proliferation, 2$^{nd}$ edition, 1998, pp. 70–84).

The modulator compound will cause an increase or a decrease in the cellular response to the IIP protein activity and will be either an activator or an inhibitor of IGF-receptor function, respectively.

Alternatively, putative modulators are added to cultures of tumor cells, and the cells display an altered morphology and/or display reduced or enhanced growth properties. A putative modulator compound is added to the cells with and without IIP protein and a cellular response is measured by direct observation of morphological characteristics of the cells and/or the cells are monitored for their growth properties. The modulator compound will cause an increase or a decrease in the cellular response to IIP protein and will be either an activator or an inhibitor of IGF-1 receptor activity, respectively.

LIST OF REFERENCES

Altschul, S. F., et al., *J. Mol. Biol.* 215 (1990) 403–410
Altschul, S. F., et al., *Nucleic Acids Res.* 25 (1997) 3389–3402
Ausubel I., Frederick M., *Current Protocols in Mol. Biol.* (1992), John Wiley and Sons, New York
Weidner, K. M., et al., *Nature* 384 (1996) 173–176;
Behrens, J., et al., *Nature* 382 (1996) 638–642
Behrens, J., et al., *Science* 280 (1998) 596–599
Boehringer Mannheim GmbH, Apoptosis and Cell Proliferation, 2nd edition, 1998, pp. 70–84
Büittner et al., *Mol. Cell. Biol.* 11 (1991) 3573–3583
Cabral, J. H., et al., *Nature* 382 (1996) 649–652
Chomczynski and Sacchi, *Anal. Biochem.* 162 (1987) 156–159
Chowdhury, K., et al., *Mech. Dev.* 39 (1992) 129–142
Cooke, M. P., and Perlmutter, R. M., *New Biol.* 1 (1989) 66–74
Database EMBL Nos. AF089818 and AF061263
Denny, P., and Ashworth, A., *Gene* 106 (1991) 221–227
DeVries, L., et al., *Proc. Natl. Acad. Sci.* USA 95 (1998) 12340–12345
Dey, R. B., et al., Mol. Endocrinol. 10 (1996) 631–641
EP-A 0 063 879
EP-A 0 128 018
EP-A 0 173 251
EP-A 0 200 362
Feinberg, A. P., and Vogelstein, B., *Anal. Biochem.* 137 (1984) 266–267
Fields, S., and Song, O., *Nature* 340 (1989) 245–246
Goulding, M. D., et al., *EMBO J.* 10 (1991) 1135–1147
Hames, B. D., Higgins, S. G., *Nucleic acid hybridisation—a practical approach* (1985) IRL Press, Oxford, England
Lehmann, J. M., et al., *Nucleic Acids Res.* 18 (1990) 1048)
Margolis, B. L., et al., *Proc. Natl. Acad. Sci.* USA 89 (1992) 8894–8898
Needleman and Wunsch, *J. Biol. Chem.* 48 (1970) 443–453
*PCR—A Practical Approach* (1991), publ. M. J. McPherson, P. Quirke, G. R. Taylor, IRL Press
Pearson, W. R., *Methods in Enzymology* 183 (1990) 63–68, Academic Press, San Diego, U.S.
Ponting, C. P., et al., *BioEssays* 19 (1997) 469–479
*PCR Protocols—A Guide to Methods and Applications* (1990), publ. M. A. Innis, D. H. Gelfand, J. J. Sninsky, T. J. White, Academic Press Inc.
Riedel, H., et al., *J. Biochem.* 122(1997) 1105–1113
Rousset, R., et al., *Oncogene* 16 (1998) 643–654
Sambrook et al., *Molecular Cloning: A laboratory manual* (1989) Cold Spring Harbor Laboratory Press, New York, USA
Smith and Waterman, *Adv. Appl. Math.* 2 (1981) 482–489
Ullrich, A., et al., *EMBO J.* 5 (1986) 2503–2512
U.S. Pat. No. 2915082
Wahl, G. M., et al., *Proc. Natl. Acad. Sci.* USA 76 (1979) 3683–3687
Weidner, K. M., et al., *Nature* 384 (1'996) 173–176
WO 97/27296
WO 89/06698
WO 95/14772
Yokouchi, M., et al., *Oncogene* 15 (1998) 7–15

What is claimed is:

1. A nucleic acid comprising a nucleic acid sequence encoding the polypeptide of SEQ ID NO:6.

2. A nucleic acid according to claim 1, wherein said nucleic acid comprises SEQ ID NO:5.

3. A recombinant expression vector for expressing a polypeptide comprising SEQ ID NO:6, the recombinant expression vector comprising a nucleic acid as claimed in claim 1.

4. A host cell transformed by a nucleic acid of claim 1.

5. A method for the production of a protein which binds to an IGF-1 receptor, the method comprising expressing an exogenous DNA in prokaryotic or eukaryotic host cells and isolation of the desired protein, wherein the exogenous DNA comprises a nucleic acid of claim 1.

* * * * *

SEQUENCE LISTING

<160> NUMBER OF SEQ ID NOS: 10

<210> SEQ ID NO 1
<211> LENGTH: 1707
<212> TYPE: DNA
<213> ORGANISM: Homo sapiens
<220> FEATURE:
<223> OTHER INFORMATION: n at position 186, 187, 203, and 205 is a, t, g, or c.

<400> SEQUENCE: 1

| | | | | | | |
|---|---|---|---|---|---|---|
| gaaacccaca | ggaggcaacc | acactagttt | agatcttctg | gtgacccac | ttctcgctgc | 60 |
| tcatgccgct | gggactgggg | cggcggaaaa | aggcgccccc | tctagtggaa | aatgaggagg | 120 |
| ctgagccagg | ccgtggaggg | ctgggcgtgg | gggagccagg | gcctctgggc | ggaggtgggt | 180 |
| cggggnncccc | ccaaatggc | ttncncccccc | ctcccccagc | cctgcggccc | cgcctcgtgt | 240 |
| tccacaccca | gctggcccat | ggcagtccca | ctggccgcat | cgagggcttc | accaacgtca | 300 |
| aggagctgta | tggcaagatc | gccgaggcct | tccgcctgcc | aactgccgag | gtgatgttct | 360 |
| gcaccctgaa | cacccacaaa | gtggacatgg | acaagctcct | gggggggccag | atcgggctgg | 420 |
| aggacttcat | cttcgcccac | gtgaaggggc | agcgcaagga | ggtggaggtg | ttcaagtcgg | 480 |
| aggatgcact | cgggctcacc | atcacggaca | acggggctgg | ctacgccttc | atcaagcgca | 540 |
| tcaaggaggg | cagcgtgatc | gaccacatcc | acctcatcag | cgtgggcgac | atgatcgagg | 600 |
| ccattaacgg | gcagagcctg | ctgggctgcc | ggcactacga | ggtggcccgg | ctgctcaagg | 660 |
| agctgccccg | aggccgtacc | ttcacgctga | agctcacgga | gcctcgcaag | gccttcgaca | 720 |
| tgatcagcca | gcgttcagcg | ggtggccgcc | ctggctctgg | cccacaactg | ggcactggcc | 780 |
| gagggaccct | gcggctccga | tcccgggggcc | ccgccacggt | ggaggatctg | ccctctgcct | 840 |
| ttgaagagaa | ggccattgag | aaggtggatg | acctgctgga | gagttacatg | ggtatcaggg | 900 |
| acacggagct | ggcagccacc | atggtggagc | tgggaaagga | caaaaggaac | ccggatgagc | 960 |
| tggccgaggc | cctggacgaa | cggctgggtg | actttgcctt | ccctgacgag | ttcgtctttg | 1020 |
| acgtctgggg | cgccattggg | gacgccaagg | tcggccgcta | ctaggactgc | ccccggaccc | 1080 |
| tgcgatgatg | acccgggcgc | aacctggtgg | gggcccccag | cagggacact | gacgtcagga | 1140 |
| cccgagcctc | cagcctgagc | ctagctcagc | agcccaagga | cgatggtgag | gggaggtggg | 1200 |
| gccaggcccc | ctgccccgct | ccactcggta | ccatcccctc | cctggttccc | agtctggccg | 1260 |
| gggtccccgg | ccccccctgtg | ccctgttccc | cacctacctc | agctgggtca | ggcacaggga | 1320 |
| ggggagggat | cagccaaatt | gggcggccac | ccccgcctcc | accactttcc | accatcagct | 1380 |
| gccaaactgg | tccctctgtc | tccctggggc | cttgggttct | gtttgggggt | catgaccttc | 1440 |
| ctagtttcct | gacgcaggga | atacagggga | gagggttgtc | cttccccccca | gcaaatgcaa | 1500 |
| taatgccctc | accctcctg | agaggagccc | cctccctgtg | gagcctgtta | cctccgcatt | 1560 |
| tgacacgagt | ctgctgtgaa | ccccgcaacc | tcctccccac | ctcccatctc | tccttccagg | 1620 |
| cccatccctg | gcccagagca | ggagggaggg | agggacgatg | gcggtggtt | tttgtatctg | 1680 |
| aatttgctgt | cttgaacata | aagaatc | | | | 1707 |

<210> SEQ ID NO 2
<211> LENGTH: 333
<212> TYPE: PRT
<213> ORGANISM: Homo sapiens
<220> FEATURE:

```
<223> OTHER INFORMATION: Xaa at position 42, 47, and 48 is any one of
      the twenty naturally occurring amino acids.

<400> SEQUENCE: 2

Met Pro Leu Gly Leu Gly Arg Arg Lys Lys Ala Pro Pro Leu Val Glu
 1               5                  10                  15

Asn Glu Glu Ala Glu Pro Gly Arg Gly Gly Leu Gly Val Gly Glu Pro
            20                  25                  30

Gly Pro Leu Gly Gly Gly Ser Gly Xaa Pro Gln Met Gly Xaa Xaa
        35                  40                  45

Pro Pro Pro Ala Leu Arg Pro Arg Leu Val Phe His Thr Gln Leu
    50                  55                  60

Ala His Gly Ser Pro Thr Gly Arg Ile Glu Gly Phe Thr Asn Val Lys
65                  70                  75                  80

Glu Leu Tyr Gly Lys Ile Ala Glu Ala Phe Arg Leu Pro Thr Ala Glu
            85                  90                  95

Val Met Phe Cys Thr Leu Asn Thr His Lys Val Asp Met Asp Lys Leu
            100                 105                 110

Leu Gly Gly Gln Ile Gly Leu Glu Asp Phe Ile Phe Ala His Val Lys
            115                 120                 125

Gly Gln Arg Lys Glu Val Glu Val Phe Lys Ser Glu Asp Ala Leu Gly
    130                 135                 140

Leu Thr Ile Thr Asp Asn Gly Ala Gly Tyr Ala Phe Ile Lys Arg Ile
145                 150                 155                 160

Lys Glu Gly Ser Val Ile Asp His Ile His Leu Ile Ser Val Gly Asp
                165                 170                 175

Met Ile Glu Ala Ile Asn Gly Gln Ser Leu Leu Gly Cys Arg His Tyr
            180                 185                 190

Glu Val Ala Arg Leu Leu Lys Glu Leu Pro Arg Gly Arg Thr Phe Thr
            195                 200                 205

Leu Lys Leu Thr Glu Pro Arg Lys Ala Phe Asp Met Ile Ser Gln Arg
    210                 215                 220

Ser Ala Gly Gly Arg Pro Gly Ser Gly Pro Gln Leu Gly Thr Gly Arg
225                 230                 235                 240

Gly Thr Leu Arg Leu Arg Ser Arg Gly Pro Ala Thr Val Glu Asp Leu
                245                 250                 255

Pro Ser Ala Phe Glu Glu Lys Ala Ile Glu Lys Val Asp Asp Leu Leu
            260                 265                 270

Glu Ser Tyr Met Gly Ile Arg Asp Thr Glu Leu Ala Ala Thr Met Val
            275                 280                 285

Glu Leu Gly Lys Asp Lys Arg Asn Pro Asp Glu Leu Ala Glu Ala Leu
            290                 295                 300

Asp Glu Arg Leu Gly Asp Phe Ala Phe Pro Asp Glu Phe Val Phe Asp
305                 310                 315                 320

Val Trp Gly Ala Ile Gly Asp Ala Lys Val Gly Arg Tyr
            325                 330

<210> SEQ ID NO 3
<211> LENGTH: 380
<212> TYPE: DNA
<213> ORGANISM: Homo sapiens
<220> FEATURE:
<223> OTHER INFORMATION: n at position 369 is a, t, g, or c.

<400> SEQUENCE: 3
gccgaggaag gagaagggc taaaccttgg agagtggatg gctcaaagga ttctcagatc   60
```

-continued

```
acacctcggg aggatcatgg gcaggagagc ctgttggcag ggctccacgg aacgcatcca      120
ccaaagacaa ggcagaaagt cactgcccaa gccggaggcc ccggggatcc catgcttttt      180
tcaagcccag agacagatga gaagcttttt atatgtgcgc agtgtggcaa aaccttcaac      240
aatacctcca acctgagaac gcaccagcgg atccacactg gcgagaagcc ctacatgtgt      300
tccgagtgtg gcaagagttt ctcccggagc tccaaccgca tccggcacga gcgcatccac      360
ctggaagana agcactctga                                                  380
```

<210> SEQ ID NO 4
<211> LENGTH: 126
<212> TYPE: PRT
<213> ORGANISM: Homo sapiens
<220> FEATURE:
<223> OTHER INFORMATION: Xaa at position 123 is any one of the twenty
      naturally occurring amino acids.

<400> SEQUENCE: 4

```
Ala Glu Glu Gly Glu Gly Ala Lys Pro Trp Arg Val Asp Gly Ser Lys
 1               5                  10                  15

Asp Ser Gln Ile Thr Pro Arg Glu Asp His Gly Gln Glu Ser Leu Leu
            20                  25                  30

Ala Gly Leu His Gly Thr His Pro Pro Lys Thr Arg Gln Lys Val Thr
        35                  40                  45

Ala Gln Ala Gly Gly Pro Gly Asp Pro Met Leu Phe Ser Ser Pro Glu
    50                  55                  60

Thr Asp Glu Lys Leu Phe Ile Cys Ala Gln Cys Gly Lys Thr Phe Asn
65                  70                  75                  80

Asn Thr Ser Asn Leu Arg Thr His Gln Arg Ile His Thr Gly Glu Lys
                85                  90                  95

Pro Tyr Met Cys Ser Glu Cys Gly Lys Ser Phe Ser Arg Ser Ser Asn
            100                 105                 110

Arg Ile Arg His Glu Arg Ile His Leu Glu Xaa Lys His Ser
        115                 120                 125
```

<210> SEQ ID NO 5
<211> LENGTH: 678
<212> TYPE: DNA
<213> ORGANISM: Homo sapiens

<400> SEQUENCE: 5

```
atgtcgagac cccggaagag gctggctggg acttctggtt cagacaaggg actatcagga      60
aaacgcacca aaactgagaa ctcaggtgag gcattagcta aagtggagga ctccaaccct     120
cagaagactt cagccactaa aaactgtttg aagaatctaa gcagccactg gctgatgaag     180
tcagagccag agagccgcct agagaaaggt gtagatgtga agttcagcat tgaggatctc     240
aaagcacagc ccaaacagac aacatgctgg gatggtgttc gtaactacca ggctcggaac     300
ttccttagag ccatgaagct gggagaagaa gccttcttct accatagcaa ctgcaaagag     360
ccaggcatcg caggactcat gaagatcgtg aaagaggctt acccagacca cacacagttt     420
gagaaaaaca atccccatta tgacccatct agcaaagagg acaaccctaa gtggtccatg     480
gtggatgtac agtttgttcg gatgatgaaa cgtttcattc ccctggctga gctcaaatcc     540
tatcatcaag ctcacaaagc tactggtggc cccttaaaaa atatggttct cttcactcgc     600
cagagattat caatccagcc cctgacccag gaagagtttg attttgtttt gagcctggag     660
gaaaaggaac caagttaa                                                   678
```

<210> SEQ ID NO 6
<211> LENGTH: 225
<212> TYPE: PRT
<213> ORGANISM: Homo sapiens

<400> SEQUENCE: 6

```
Met Ser Arg Pro Arg Lys Arg Leu Ala Gly Thr Ser Gly Ser Asp Lys
  1               5                  10                  15

Gly Leu Ser Gly Lys Arg Thr Lys Thr Glu Asn Ser Gly Glu Ala Leu
             20                  25                  30

Ala Lys Val Glu Asp Ser Asn Pro Gln Lys Thr Ser Ala Thr Lys Asn
         35                  40                  45

Cys Leu Lys Asn Leu Ser Ser His Trp Leu Met Lys Ser Glu Pro Glu
 50                  55                  60

Ser Arg Leu Glu Lys Gly Val Asp Val Lys Phe Ser Ile Glu Asp Leu
 65                  70                  75                  80

Lys Ala Gln Pro Lys Gln Thr Thr Cys Trp Asp Gly Val Arg Asn Tyr
                 85                  90                  95

Gln Ala Arg Asn Phe Leu Arg Ala Met Lys Leu Gly Glu Glu Ala Phe
            100                 105                 110

Phe Tyr His Ser Asn Cys Lys Glu Pro Gly Ile Ala Gly Leu Met Lys
            115                 120                 125

Ile Val Lys Glu Ala Tyr Pro Asp His Thr Gln Phe Glu Lys Asn Asn
130                 135                 140

Pro His Tyr Asp Pro Ser Ser Lys Glu Asp Asn Pro Lys Trp Ser Met
145                 150                 155                 160

Val Asp Val Gln Phe Val Arg Met Met Lys Arg Phe Ile Pro Leu Ala
                165                 170                 175

Glu Leu Lys Ser Tyr His Gln Ala His Lys Ala Thr Gly Gly Pro Leu
            180                 185                 190

Lys Asn Met Val Leu Phe Thr Arg Gln Arg Leu Ser Ile Gln Pro Leu
            195                 200                 205

Thr Gln Glu Glu Phe Asp Phe Val Leu Ser Leu Glu Glu Lys Glu Pro
    210                 215                 220

Ser
225
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:primer
      TIP2c-s

<400> SEQUENCE: 7
gaaacccaca ggaggcaa                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer
      TIP2b-r

<400> SEQUENCE: 8
ggtcatcatc gcagggtc                                                18

```
<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:primer
      Hcthy-s

<400> SEQUENCE: 9
agcttgcggc cgcagatgtc gagacccgg aag                              33

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:primer
      Hcthy-r

<400> SEQUENCE: 10
agcttgcggc cgcgaattct taacttggtt ccttttcctc                      40
```